US006012452A

United States Patent [19]

Pagan

[11] Patent Number: 6,012,452

[45] Date of Patent: Jan. 11, 2000

[54] LARYNGEAL MASK ASSEMBLIES

[75] Inventor: Eric Pagan, Hythe, United Kingdom

[73] Assignee: Smiths Industries Public Limited Company, London, United Kingdom

[21] Appl. No.: 09/168,115

[22] Filed: Oct. 8, 1998

[30] Foreign Application Priority Data

Oct. 16, 1997 [GB] United Kingdom ................... 9721840

[51] Int. Cl.[7] ..................................................... A61M 16/00

[52] U.S. Cl. ................................ 128/200.26; 128/207.15

[58] Field of Search ......................... 128/200.26, 207.15; 604/96

[56] References Cited

U.S. PATENT DOCUMENTS

| | | | |
|---|---|---|---|
| 3,640,282 | 2/1972 | Kamen et al. | 128/207.15 |
| 3,799,173 | 3/1974 | Kamen | 128/207.15 |
| 4,995,388 | 2/1991 | Brain | 128/207.15 |
| 5,241,956 | 9/1993 | Brain | 128/207.15 |
| 5,249,571 | 10/1993 | Brain | 128/207.14 |
| 5,277,178 | 1/1994 | Dingley | 128/200.26 |
| 5,282,464 | 2/1994 | Brain | 128/207.15 |
| 5,297,547 | 3/1994 | Brain | 128/207.15 |
| 5,303,697 | 4/1994 | Brain | 128/200.26 |
| 5,305,743 | 4/1994 | Brain | 128/207.15 |
| 5,342,858 | 8/1994 | Litchholt et al. | 521/98 |
| 5,355,879 | 10/1994 | Brain | 128/207.15 |
| 5,391,248 | 2/1995 | Brain | 128/207.15 |
| 5,392,774 | 2/1995 | Sato | 128/207.15 |
| 5,477,851 | 12/1995 | Callaghan et al. | 128/207.15 |
| 5,513,627 | 5/1996 | Flam | 128/207.15 |
| 5,623,921 | 4/1997 | Kinsinger et al. | 128/207.15 |
| 5,771,888 | 6/1998 | Keim | 128/207.15 |
| 5,771,889 | 6/1998 | Pegan | 128/200.26 |
| 5,819,733 | 10/1998 | Bertram | 604/96 |

FOREIGN PATENT DOCUMENTS

| | | |
|---|---|---|
| 0 072 230 | 2/1983 | European Pat. Off. . |
| 072230 | 2/1983 | European Pat. Off. . |
| 448878 | 10/1991 | European Pat. Off. . |
| 43 39 706 | 4/1995 | Germany . |
| 1308882 | 3/1973 | United Kingdom . |
| 2111394 | 7/1983 | United Kingdom . |
| 2128561 | 5/1984 | United Kingdom . |
| 2205499 | 12/1988 | United Kingdom . |
| 2249959 | 5/1992 | United Kingdom . |
| 2267034 | 11/1993 | United Kingdom . |
| 2298797 | 9/1996 | United Kingdom . |
| WO 95/33506 | 12/1995 | WIPO . |
| WO 98/16273 | 4/1998 | WIPO . |
| WO 98/50096 | 11/1998 | WIPO . |

*Primary Examiner*—Aaron J. Lewis
*Attorney, Agent, or Firm*—Pollock, Vande Sande & Amernick

[57] ABSTRACT

A laryngeal mask airway has a foam cuff formed on the patient surface of a plate attached at the patient end of a tube. The cuff is of a self-skinning foam so that the skin of the foam forms the outer surface of the cuff and seals with the plate. An air lumen extruded along the tube opens at one end into the interior of the cuff and at the other end connects with an air line. The cuff can be compressed for insertion and removal by applying suction to the air line.

6 Claims, 2 Drawing Sheets

12 10 14 1 13 15 3 2 22 20 18 21 4 26 26 16 25 24

LARYNGEAL MASK ASSEMBLIES

BACKGROUND OF THE INVENTION

This invention relates to laryngeal mask assemblies.

It is common practice to use an airway known as a laryngeal mask or airway for administering anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. No. 5,355,879, U.S. Pat. No. 5,305,743, U.S. Pat. No. 5,297,547, U.S. Pat. No. 5,282,464, GB 2267034, U.S. Pat. No. 5,249,571, U.S. Pat. No. 5,241,956, U.S. Pat. No. 5,303,697, GB 2249959, GB 2111394, EP 448878, U.S. Pat. No. 4,995,388, GB 2205499, GB 2128561 and GB 2298797. WO 98/16273 describes a laryngeal airway with a foam pad that is squeezed to compress it for introduction and that gradually expands when in position.

Laryngeal masks have several advantages over endotracheal tubes, which are longer and seal with the trachea below the vocal folds. One problem with laryngeal mask airways, however, is that it is difficult to provide the cuff, which is of relatively complex shape, at low cost.

BRIEF SUMMARY OF THE INVENTION

It is an object of the present invention to provide an improved laryngeal mask assembly.

According to one aspect of the present invention there is provided a laryngeal mask assembly comprising a tube with a mask portion at its patient end, the tube opening into the center of the mask portion, the mask portion including a mount member joined with the patient end of the tube and having an outwardly-projecting plate member, the assembly including a cuff formed of a foam material attached with the plate member, the outer surface of the cuff being provided by a skin of the foam, the skin being sealed with the plate member, and the assembly including an air passage opening into the cuff by which suction can be applied to the cuff to compress it for insertion.

The air passage is preferably provided at least in part by a lumen extruded along the tube. The skin of the foam may be sealed around an edge of the plate member by welding. The assembly may include a cuff of foam extending on both sides of the plate member. The air passage may be connectable with the bore through the tube such that the cuff is inflated slightly during positive ventilation.

A laryngeal mask airway assembly according to the present invention, will now be described, by way of example, with reference to the accompanying drawings.

DETAILED DESCRIPTION OF THE PREFERRED EMBODIMENTS

Figure 1:
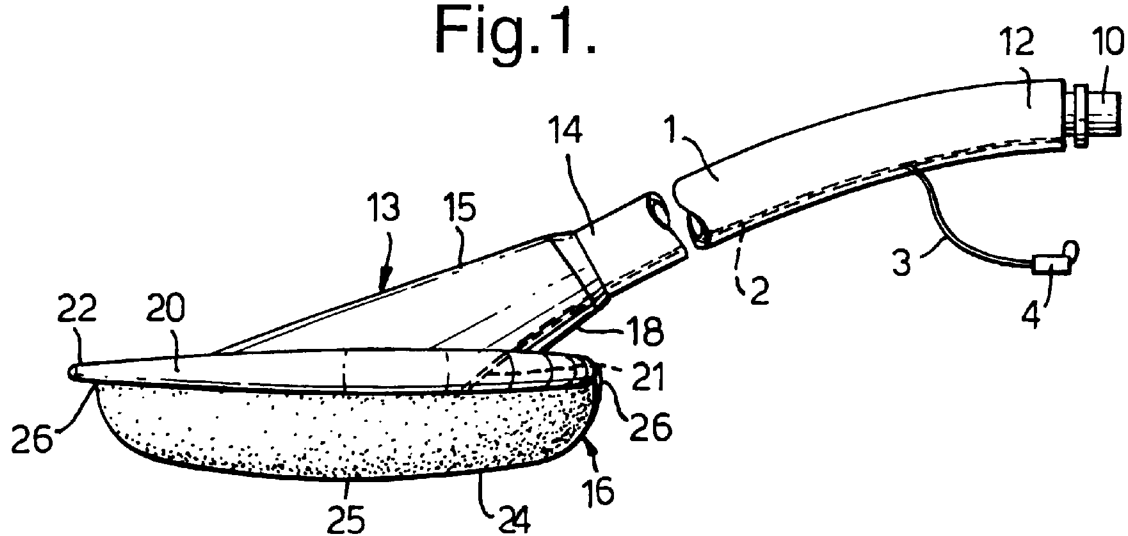
FIG. 1 is a side elevation view of the assembly with the cuff expanded.
Figure 2:
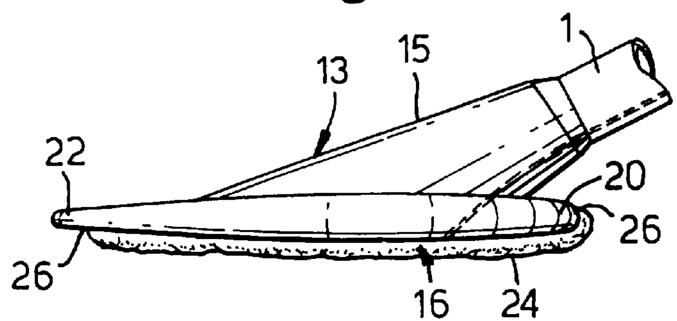
FIG. 2 is a side elevation view of the patient end of the assembly with the cuff compressed.
Figure 3:
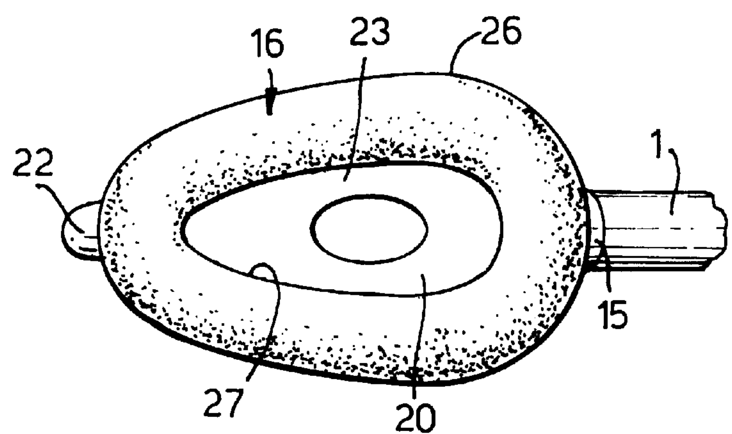
FIG. 3 is an end view of the patient end of the assembly.

With reference first to FIGS. 1 to 3, the assembly comprises a bendable tube 1 of a plastics material, such as PVC, with a coupling 10 at its machine end 12. The tube 1 is curved along its length and has a mask portion 13 attached at its patient end 14.

The tube 1 is extruded with a small bore lumen 2 within its wall. The lumen 2 is connected towards the machine end of the assembly to an air line 3, which is terminated with a connector 4. The opposite, patient end of the lumen 2 opens into the mask portion 13.

The mask portion 13 comprises a mount member 15 and a cuff member 16. The mount member 15 is moulded from a bendable plastics material, such as PVC. The mount member 15 has a hollow cylindrical sleeve 18 at its rear end, in which the forward, patient end 14 of the tube 1 is inserted and joined. A substantially flat plate 20 with a generally elliptical or egg-shape outline projects outwardly of the sleeve 18 at an angle of about 30°, at the patient end of the mount 15. An air vent hole 21 extends through the thickness of the plate 20 and communicates with the lumen 2 on the machine side of the plate. The forward end of the plate 20 is provided with a small projecting tip 22 to aid insertion and location of the patient end of the assembly.

The cuff member 16 is a ring or annulus with the same shape as the periphery of the plate 20 and with a hollow center 23 through which the tube 1 opens at the patient end of the assembly. The cuff member 16 is formed entirely from an open cell foam material, such as polyurethane, having a self skinning characteristic, so that a skin 24 forms during curing of the foam material and provides the external surface of the cuff itself, that is, the surface that contacts patient tissue during use. The cuff 16 is formed and attached with the patient (anterior) surface of the plate 20 in a simple one-step operation. The mount member 15 is loaded in a mould (not shown) with the patient side surface of the plate 20 facing into a cavity having the desired shape of the expanded cuff. The foam material is then injected in liquid form into the cavity so that it flows over the surface of the plate 20. When the foam has cured sufficiently, the mount member 15 is removed. The foam attaches to the plate 20 and, where it is exposed, forms the impervious skin 24. Although the drawings show the expanded patient face 25 of the cuff 16 as being of a relatively simple, convex shape, it can be easily made in considerably more complex shapes, simply by appropriately shaping the cavity in the mould. The cuff 16 is shaped so that it forms an effective seal with the pharynx or hypopharynx.

To ensure a gas-tight seal between the plate 20 and the cuff 16, it is preferable for the skin 24 of the cuff to be welded or otherwise sealed to the plate around its outer periphery 26 and around its inner periphery 27 around the hollow center 23 of the cuff.

The lumen 2 opens into the foam of the cuff 16 via the air vent 21 in the plate 20 and, since the foam of the cuff has open cells, it enables the cuff to be deflated or compressed by attaching a syringe to the connector 4 and withdrawing air from the cuff via the lumen 2 and the air line 3. This sucks the skin 24 of the cuff 16 closer to the plate 20, as shown in FIG. 2, giving the cuff a slimmer profile for insertion and removal from the patient. This ensures that the cuff 16 remains fully compressed during insertion and that it can be rapidly expanded when correctly positioned. Because the cuff can also be fully deflated or compressed after use, it makes removal easier and less traumatic that if the cuff remained in its expanded state.

Figure 4:
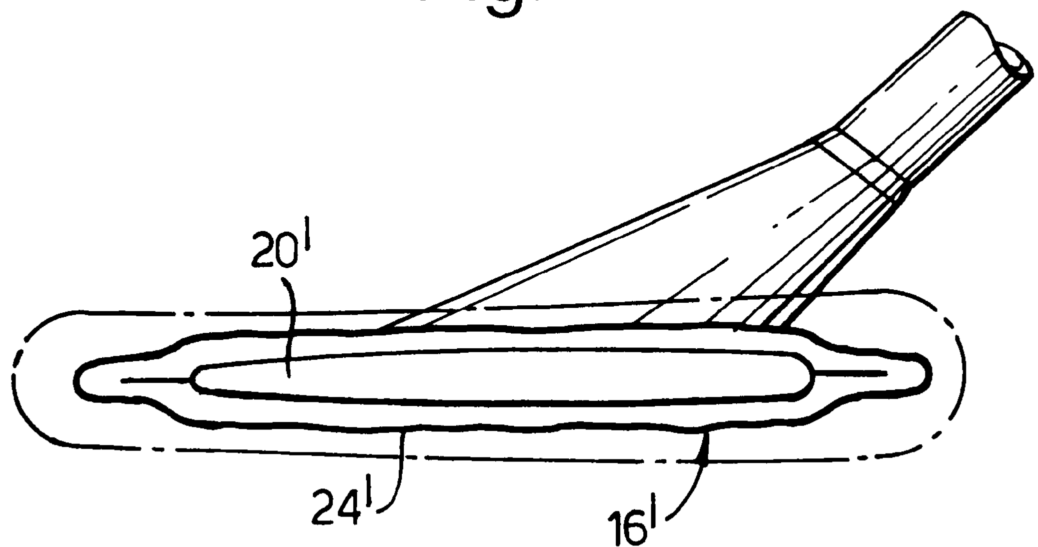
FIG. 4 is a partly-sectional side elevation view of the patient end of an alternative assembly in a compressed state.
Figure 5:
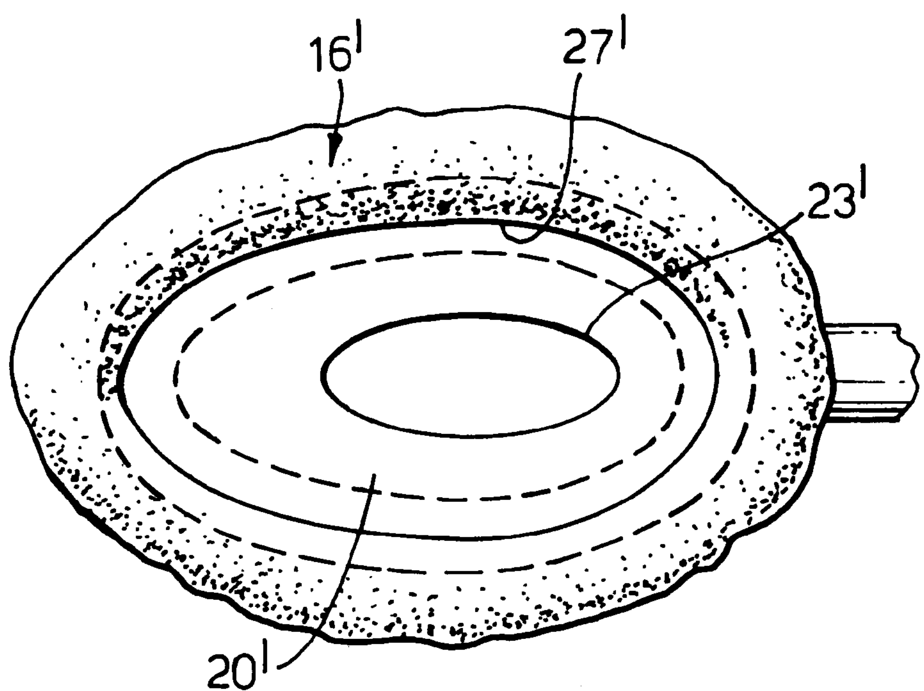
FIG. 5 is an end view of the patient end of the assembly of FIG. 4.

With reference now to FIG. 4, there is shown a similar assembly having a cuff member 16' extending over both surfaces of the plate 20' of the mount member, the expanded shape of the cuff being shown in broken outline. The edges of the cuff 16' overlap the edges of the plate 20' around its circumference. In this example, the skin 24' of the cuff 16' is welded around the periphery 27' of the center 23' on the patient side of the plate. In its natural shape, as shown by the broken line, the cuff 16' forms a thick layer over the patient (anterior) and machine (posterior) sides of the plate 20'. When deflated to the position shown, the cuff 16' is pulled close to the patient and machine sides of the plate 20' for insertion and removal.

The interior of the cuff member 16, 16' could be arranged to communicate with the main bore of the tube 1' so that, when the patient is being ventilated by positive pressure, the interior of the cuff is inflated slightly each cycle by the ventilation gas so as to form a better seal with the surrounding tissue. The arrangement by which this is achieved could be as described in EP 0072230A where the connector on the air line is removably connectable to a port opening into the machine end coupling.

What I claim is:

1. A laryngeal mask assembly including a tube and a mask portion at a patient end of said tube, said mask portion comprising a mount member joined with said patient end of said tube and said tube opening into a center of said mask portion, said mount member having an outwardly-projecting plate member and a foam cuff attached with said plate member, the improvement wherein said cuff is provided by a self-skinning foam material that forms a skin which itself provides an outer surface of said cuff, said skin of the foam material being sealed with said plate member, said assembly having an air passage opening into said cuff by which suction can be applied to said cuff to compress it for insertion.

2. A laryngeal mask assembly according to claim 1, wherein said air passage is provided at least in part by a lumen extruded along said tube.

3. A laryngeal mask assembly according to claim 1, wherein the said skin of the foam material is sealed around an edge of said plate member by welding.

4. A laryngeal mask assembly according to claim 1, wherein said plate member has two opposite sides, and wherein the foam material of said cuff extends on both sides of said plate member.

5. A laryngeal mask assembly according to claim 1, wherein the said air passage is connectable with a bore through said tube such that said cuff is inflated slightly during positive ventilation.

6. A laryngeal mask assembly comprising: a tube; an air passage extending along said tube; a mount member joined with a patient end of said tube, said mount member having an outwardly-projecting plate member; a generally elliptical cuff attached with said plate member such that said tube opens into a center of said cuff, said cuff being provided by a self-skinning foam material that forms a skin which itself provides an outer surface of said cuff, said skin of the foam material being sealed with said plate member, and said air passage opening into said cuff between said plate member and said skin such that suction can be applied to said cuff to compress it for insertion.

* * * * *